US008483795B2

(12) United States Patent
Okada

(10) Patent No.: US 8,483,795 B2
(45) Date of Patent: Jul. 9, 2013

(54) PRIMARY SOURCE MIRROR FOR BIOMAGNETOMETRY

(75) Inventor: Yoshio Okada, Boston, MA (US)

(73) Assignee: Moment Technologies, LLC, Boston, MA (US)

(*) Notice: Subject to any disclaimer, the term of this patent is extended or adjusted under 35 U.S.C. 154(b) by 0 days.

(21) Appl. No.: 13/040,027

(22) Filed: Mar. 3, 2011

(65) Prior Publication Data

US 2012/0226135 A1 Sep. 6, 2012

(51) Int. Cl.
*A61B 5/05* (2006.01)

(52) U.S. Cl.
USPC .......................................... 600/409; 600/407

(58) Field of Classification Search
USPC ................ 600/409, 12, 407; 324/244, 200, 324/204, 248, 260
See application file for complete search history.

(56) References Cited

U.S. PATENT DOCUMENTS

| | | | |
|---|---|---|---|
| 5,494,033 A | 2/1996 | Buchanan et al. | |
| 5,938,598 A | 8/1999 | Takeda et al. | |
| 6,226,538 B1 | 5/2001 | Kugai et al. | |
| 6,815,949 B2 | 11/2004 | Kandori et al. | |
| 7,002,341 B2 | 2/2006 | Baudenbacher et al. | |
| 7,197,352 B2 | 3/2007 | Gott et al. | |
| 7,262,597 B2 | 8/2007 | Woods et al. | |
| 7,403,809 B2 | 7/2008 | Tsukada et al. | |
| 7,589,525 B2 * | 9/2009 | Woodard et al. | 324/239 |
| 7,672,707 B2 | 3/2010 | Takeda | |
| 7,729,740 B2 | 6/2010 | Kraus, Jr. et al. | |
| 7,756,564 B2 | 7/2010 | Matsui et al. | |
| 2007/0239059 A1 | 10/2007 | McIver | |

OTHER PUBLICATIONS

Phys. Med. Biol., 1987, vol. 32, No. 8, 933-970. The passive electrical properties of biological systems: their significance in physiology, biophysics and biotechnology Ronald Pethig and Douglas B KellS Institute of Molecular and Biomolecular Electronics, University College of North Wales, Dean Street, Bangor.*
Clinical Neurophysiology 116 (2005) 799-806 Evaluation of commercially available electrodes and gels for recording of slow EEG potentials P. Tallgrena, S. Vanhataloa,b, K. Kailaa, J. Voipioa, Department of Biological and Environmental Sciences, University of Helsinki, P.O. Box 65, 00014 Helsinki, Finland Department of Clinical Neurophysiology.*
Understanding the Properties of Matter Michael De Podesta Edition 2, illustrated, revised Publisher CRC Press, 2002 ISBN 0415257883, 9780415257886.*
Judge, Arthur W. Aircraft and Automobile Materials of Construction, vol. II, Nonferrous and Organic Materials. London: Pitman, 1921: 477.*
Structural State and Diffusion in a Silicate Glass by R. J. Charles Research laboratory, General Electric Company, Schenectady, New York Journal of the American Ceramic SocietyVol. 45, Issue 3, Article first published online: Jun. 2, 2006.*

(Continued)

Primary Examiner — Long V Le
Assistant Examiner — Michael Kellogg
(74) Attorney, Agent, or Firm — The Maxham Firm

(57) ABSTRACT

Apparatus and methods to enable the complete detection and assessment of electric currents flowing in a conductive medium not only parallel, but also perpendicular to the boundary separating the conducting medium from a nonconducting medium by means of a magnetometer located outside of the conducting medium itself.

23 Claims, 4 Drawing Sheets

OTHER PUBLICATIONS

CVD Diamond—a new Technology for the Future? Paul W. May School of Chemistry, University of Bristol, Cantock's Close, Bristol BS8 1TS, U.K. This is an article which appeared in Endeavour Magazine 19(3), (1995) pp. 101-106. (© copyright Elsevier, 1995).*

Biomagnetism using SQUIDs: status and perspectives Karsten Sternickel1 and Alex I Braginski2 CardioMag Imaging, Inc., 450 Duane Avenue, Schenectady, NY 12304, USA 2 Research Center Julich, ISG-2, D-52425 Julich, Germany.*

Title an Introduction to Error Analysis: The Study of Uncertainties in Physical Measurements Physics—chemistry—engineering A series of books in physics Author John Robert Taylor Edition 2 Publisher University Science Books, 1997 ISBN 093570275X, 9780935702750.*

International Search Report (PCT/US2012/026476, Feb. 24, 2012); 3 pages.

D. Cohen et al., "Magnetic Field Produced by a Current Dipole," J. Electrocardiology, 9 (4), pp. 409-417 (1976).

F. Grynszpan et al., "Model Studies of the Magnetogardiogram," Biophysical Journal, vol. 13, pp. 911-925 (1973).

Y. Okada et al., "Magnetic Evoked Field Associated With Transcortical Currents in Turtle Cerebellum," Biophys. J., vol. 53, pp. 723-731 (1988).

R. Plonsey, "Generation of Magnetic Fields by the Human Body (Theory)," Biomagnetism, Berlin, De Gruyter, pp. 177-205 (1981).

* cited by examiner

PRIMARY SOURCE MIRROR FOR BIOMAGNETOMETRY

FIELD OF INVENTION

The present application relates generally to the field of measuring the magnetic fields produced by naturally occurring electric currents which flow in the brain and other organs of humans and animals, in tissue slices and cultures made from these organs, in cells harvested from these tissues, and more particularly to the apparatus and methods for making such measurements.

BACKGROUND OF THE INVENTION

The term magnetoencephalography (often abbreviated by the acronym "MEG") refers to the detection and measurement of the magnetic fields which are produced by the electric currents which flow naturally within the bodies of humans and animals. For example, such electric current flows are a fundamental feature of the functioning of the neurological system of a human being. Charged ionic flows within the neurons which make up part of the human brain are, in effect, an electric current which produces a magnetic field which can be measured using the methods of MEG. The electric currents which drive the pumping of the heart in an animal produce magnetic fields which can be measured using magnetocardiography. Measurements of the magnetic fields produced by these electric currents can be used to deduce information about the size and direction of the currents as a function of time as well as their location and distribution within the body of a person, and therefore to provide information about the state of health and the state of function of the person.

Apparatus and methods of MEG have been developed and expanded over the past forty years, enhancing sensitivity to enable the detection of magnetic fields produced by electric currents flowing deep within the body. The "field of view" of the magnetometers used for MEG have been systematically expanded from single channel detectors of the magnetic field at one location to large helmet-shaped systems measuring the values of the magnetic fields at up to 275 locations around the head of a human being or up to 150 locations over the chest of a human being.

Magnetoencephalography has also been used to measure magnetic fields produced by electric currents flowing in biologic samples such as brain tissue slices of laboratory animals. In these systems, methods have been developed to bring the detector of the magnetic field as close as possible to the electric current itself to maximize the size of the measured signal and the ratio of the signal to the background magnetic noise. In some case, spacing as small as 1 mm or less have been achieved.

Generally, the biomagnetic measurements of biogenic electric currents are useful for measuring the distribution of such currents in a tissue such as a brain slice or in an organ such as a brain or heart.

One major limitation in the application of the biomagnetic techniques for the purposes outlined above arises from a fundamental property of magnetic fields produced by electric currents flowing in tissues or organs. Any such tissues or organs can be described by a circuit of electrically active cells that produce the biogenic current. In intact humans or animals the tissue of the organ that contains such electrogenic cells is saturated with physiological saline. In in vitro preparations, such a tissue is immersed in a bath of physiological saline. The physiological saline conducts electricity; thus, the medium containing the saline such as the brain or the head, or a bath containing the tissue, is called "conductive medium." From the fundamental principles governing electromagnetism in conductive media, an electric current which flows within and proximate to the surface of such a conductive medium and flows in a direction which is perpendicular to the surface of that medium produces no net magnetic field external to the medium itself. This is strictly true when the conducting medium is spherical or flat. A large bath can be thought of as a part of an infinitely large sphere. But, it is very well approximated even in a conducting medium that lacks a spherical symmetry when the cells are close to the boundary separating the conducting medium from the surrounding non-conducting medium. This factor has limited the utility of biomagnetic measurements such as MEG in providing complete information about electric currents in a tissue or in an organ. The conventional biomagnetic techniques can provide the information only about those components of the electric currents flowing within conducting media which flow in a direction parallel to the surface of that medium, but not the currents which flow normal to the surface. In particular, this factor has impacted heavily on the application of MEG to examine the brains of prematurely born human babies, since in these babies the cerebral cortex is poorly developed and larger percentages of neuronal activity are perpendicular to the surface of the skull and cannot be easily detected with conventional biomagnetic techniques. In general, this factor has significantly constrained the application of the biomagnetic techniques for measuring biogenic currents from human and animal brains.

SUMMARY OF EMBODIMENTS OF THE INVENTION

Accordingly, it is a purpose of embodiments of the present invention to provide apparatus and methods for enabling the detection and assessment of all components of the biogenic currents, including the electric current flowing in a conductive medium in a direction perpendicular to the boundary surface separating a conducting medium (for example, a head or a saline bath) from the non-conducting medium (for example, air) by means of a magnetometer located outside of the medium itself. The use of these embodiments will therefore enable a more complete assessment of all components of electric currents which flow within a conductive medium.

The following summary of embodiments of the invention is provided to enable an understanding of some of its novel features but is not intended to be a full description. A full appreciation of the aspects of the various embodiments will be provided by the specification, claims, drawings, and abstract as a whole.

One feature of the invention is to provide a structure which provides a secondary source of magnetic field which is induced by and reflects a primary electric current flowing in a conductive medium. Detection and measurement of the magnetic field produced by the secondary source will provide information about the size and location of the primary electric current that is oriented perpendicular to the boundary surface separating the conducting medium from the non-conducting medium (such as air). Here, the primary current source of biomagnetic field is a cell or a group of cells that produce the electric current, and a secondary current source is a source of magnetic field in the conducting medium produced by the primary source. The secondary source in general exists at boundary surfaces separating regions differing in electrical conductivity. Secondary sources generate magnetic fields that are directly related to the current in the primary source. Thus, it is possible to indirectly measure the primary current perpendicular to the boundary surface, which is otherwise not detectable with conventional biomagnetometry.

A further feature of the invention is to provide an apparatus and method which enables an expanded capability to detect and assess electric currents flowing within the brain and body of human beings and animals.

A further feature of the invention is to provide an apparatus and method which enables an expanded capability to detect and measure electric currents flowing in specimens of neurological tissue from humans and animals where such measurements are conducted on the specimens in vitro.

A further feature of the invention is to provide an apparatus and method which enables an expanded capability to perform functional assessments of the brains of neonates and other very young human beings by means of MEG.

BRIEF DESCRIPTION OF THE DRAWING

The objects, advantages, features, and other desirable characteristics of embodiments of the invention can be readily perceived from the following detailed description and attached drawing, in which.

DETAILED DESCRIPTION OF EMBODIMENTS OF THE INVENTION

It is a fundamental property of the physics of electromagnetism that, at the boundary between a conductive medium and a non-conductive medium, an electric current which is flowing within the conductive medium and in a direction parallel to the boundary produces a magnetic field that extends throughout both the conductive and non-conductive media. However, an electric current which is flowing within the conductive medium and in a direction orthogonal to the boundary produces a magnetic field which extends throughout the conductive medium but produces no magnetic field in the non-conductive medium. This is strictly true for a conducting medium having a spherical symmetry such as a sphere or a semi-infinitely large saline bath. The human head is nearly spherical, at least over a large dorsal portion of the head. A large bath containing a tissue immersed in a physiological saline approximates an infinitely large bath. In these cases the approximation is excellent (see F. Grynszpan and D. B. Geselowitz, Biophysics Journal, Vol 13, pp. 911-925 (1973); also D. Cohen and H. Hosaka, J. Electrocardiol., 1976, Vol. 9, pp. 409-417 (1976); also Y. C. Okada and C. Nicholson, Biophys. J., Vol. 53, pp. 723-731 (1988)).

One effective means for determining the characteristics of an electric current flowing in a conductive medium—location, amplitude, direction of flow as a function of time—is by measuring the magnetic field produced by that current. However, because magnetic fields external to the conductive medium are only produced by those currents which flow in a direction parallel to the surface or boundary of the medium, this method is strongly limited. Placing a magnetic field detector within the conductive medium itself is a potential approach but faces numerous practical difficulties. Placing a magnetic field detector external to the conductive medium limits this method to determining the characteristics only for the electric current components which are parallel to the surface of the medium.

Figure 1:
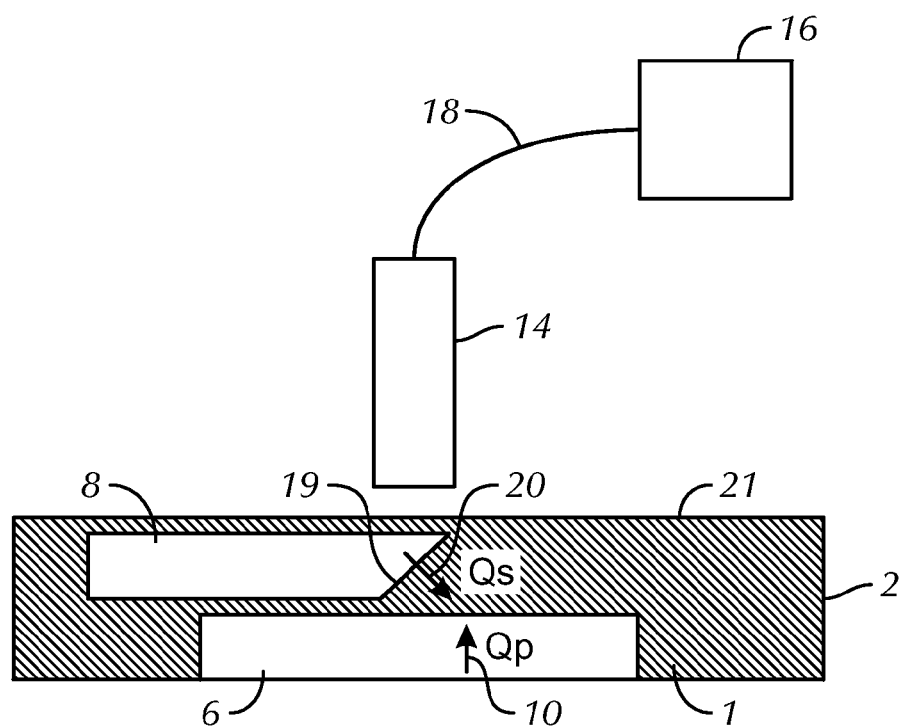
FIG. 1 is a schematic view of an apparatus which enables the detection and measurement of the magnetic field produced by electric currents flowing in a biologic sample located in a conductive material (for example, a liquid or a gel) in accordance with an embodiment of the invention.

All embodiments of the current invention are aimed at alleviating this limitation. In FIG. 1, a biologic sample 6 is shown immersed in a conductive solution 1 contained within a vessel 2. A preferred embodiment would use a saline solution as a conductive solution. An alternative could use an agar soaked with physiological saline. Small electric current elements flowing within the biologic sample can be represented as "current dipoles," each of which is characterized by a current amplitude and direction of flow and a length between a source and a sink between which the current flows. For example, if the biologic sample were a slice of brain tissue containing a neuron, the functioning of that neuron could be characterized by an electric current flowing through the neuron, and the "equivalent current dipole" representation of that functioning would include the spatial position and orientation of the neuron and the current amplitude between a source and a sink in the neuron. In the biologic sample in FIG. 1, an equivalent primary current dipole in a population of vertically oriented neurons is represented by arrow 10. Any current dipole within the sample can be expressed by basic vector mathematics as the sum of two components, one component oriented along the direction perpendicular to the surface of the sample and one component oriented in a direction parallel to the surface of the sample. In FIG. 1, current dipole $Q_p$ 10 is oriented perpendicularly to the surface of biologic sample 6. Placed above the top surface of the biologic sample and within conductive medium 1 is non-conductive solid 8 having flat face 19 at one end. In a preferred embodiment, the non-conductive solid is cylindrical in cross-section and has a face at one end which is flat and at an angle approximately 45 degrees from being parallel with the upper surface of the sample. The 45 degree face is positioned approximately above primary current dipole 10. A preferred material for the non-conductive solid is glass. Alternative materials from which the non-conductive solid can be fabricated include, but are not limited to, sapphire, quartz, diamond, and filled composite plastics.

Figure 2:
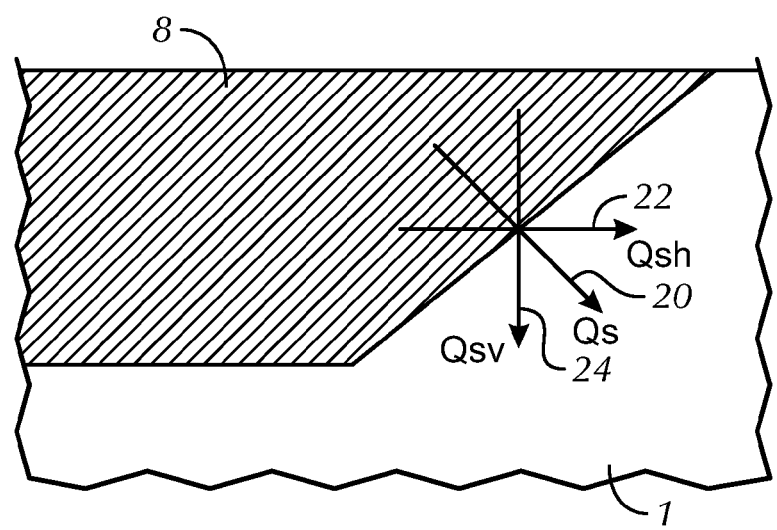
FIG. 2 is an enlarged schematic view of the non-conductive structure of FIG. 1 in which a secondary source is induced by a primary electric current.

According to the theory of secondary sources in conductive and non-conductive media, a secondary source of magnetic field $Q_s$ 20 is induced on surface 19 of the non-conductive solid by primary current dipole 10 (see, for example, R. Plonsey in *Biomagnetism*, Berlin, De Gruyter, pp. 177-205 (1981)). This secondary dipolar source is positioned on the boundary surface of the non-conductive solid oriented perpendicular to face 19 of the non-conductive solid. Surface 19 may be referred to as a primary source mirror or PRISM. FIG. 2 shows a fragment of non-conductive solid 8 and secondary source 20 induced by primary current 10. Secondary source 20 can be resolved into two components by simple vector physics, one component, represented by arrow 22, being parallel and the other component, represented by arrow 24, being perpendicular to surface 21 of conducting medium 1 in FIG. 1. Since component 22 is parallel to surface 21, it produces a net magnetic field above the conductive medium which can be detected and measured by a magnetic field sensor or magnetometer 14. The output from magnetometer 14 is transmitted to a data acquisition and analysis system 16 via cable 18. This apparatus then produces values of the magnetic field produced by secondary source magnetic field 20 which is induced by primary current dipole 10. This value provides information, such as location and current amplitude as a function of time, characterizing the primary current. As the primary current changes its amplitude in time, the values of the magnetic field will change as well. Frequency response available via this method utilizing secondary sources will be comparable to the frequencies exhibited by the primary current. The position of the non-conductive solid can be changed to provide additional information about primary current 10 such as the volume of the active tissue in sample 6.

A typical apparatus such as that described above for use in a biomagnetic application would consist of: 1) vessel 2, which may be a petri dish with diameter of approximately 5 cm and depth of about 5 mm; 2) biologic sample 6 having thickness of about 0.01 to 0.4 mm; 3) an oxygenated physiological saline solution as a conductive medium filling the petri dish to the rim; 4) a cylindrical glass rod of diameter approximately 1 mm and length of about 2 mm as the non-conductive solid 8 with one end sealed and polished to form surface 19 (PRISM) at an angle of approximately 45 degrees from the axis of the cylindrical glass rod; and 5) wherein magnetometer 14 has a sensitivity to magnetic fields of at least 100 femtoTesla per root Hertz. However, a variety of types of magnetometers may be used to detect the magnetic field produced by one or more secondary sources, depending on the strength of the secondary source. Hall effect magnetometers, flux gate magnetometers, pumped optical or atomic magnetometers, and SQUID-based magnetometers, amongst others, are all candidates for use in this apparatus.

Figure 3:
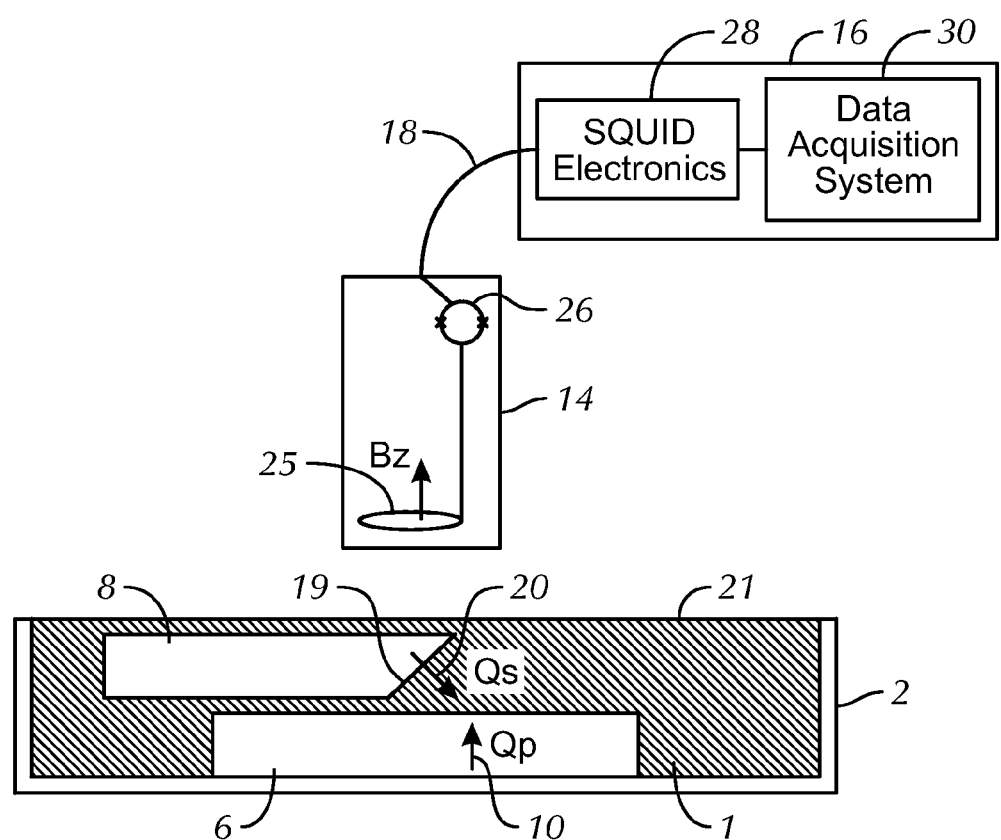
FIG. 3 is a schematic diagram of the apparatus of FIG. 1 wherein the magnetic fields are detected and measured by means of a superconducting magnetometer, in accordance with an embodiment of the invention.

A preferred embodiment of the configuration illustrated in the foregoing is shown in FIG. 3. In this figure, magnetometer 14 is a superconducting magnetometer which utilizes a superconducting quantum interference device or SQUID to provide a greater sensitivity to the magnetic fields than other types of magnetometers. This type of magnetometer is well known. See, for example, Tsukada et al., U.S. Pat. No. 7,403,809, which discloses a magnetometer of this type. In this embodiment, the magnetic field produced by secondary source 20 induces a current in pickup coil 25 located within the magnetometer 14. That current is coupled to SQUID device 26 within the magnetometer. The output of the SQUID device, which is a measure of the magnetic field produced by the secondary source, is transmitted via cable 18 to SQUID electronics 28 and data acquisition system 30 in data acquisition and analysis system 16.

The embodiment shown in FIG. 3 and described above is a preferred embodiment for measuring electric currents flowing in tissue samples which lend themselves to immersion in a conductive bath.

Figure 4:
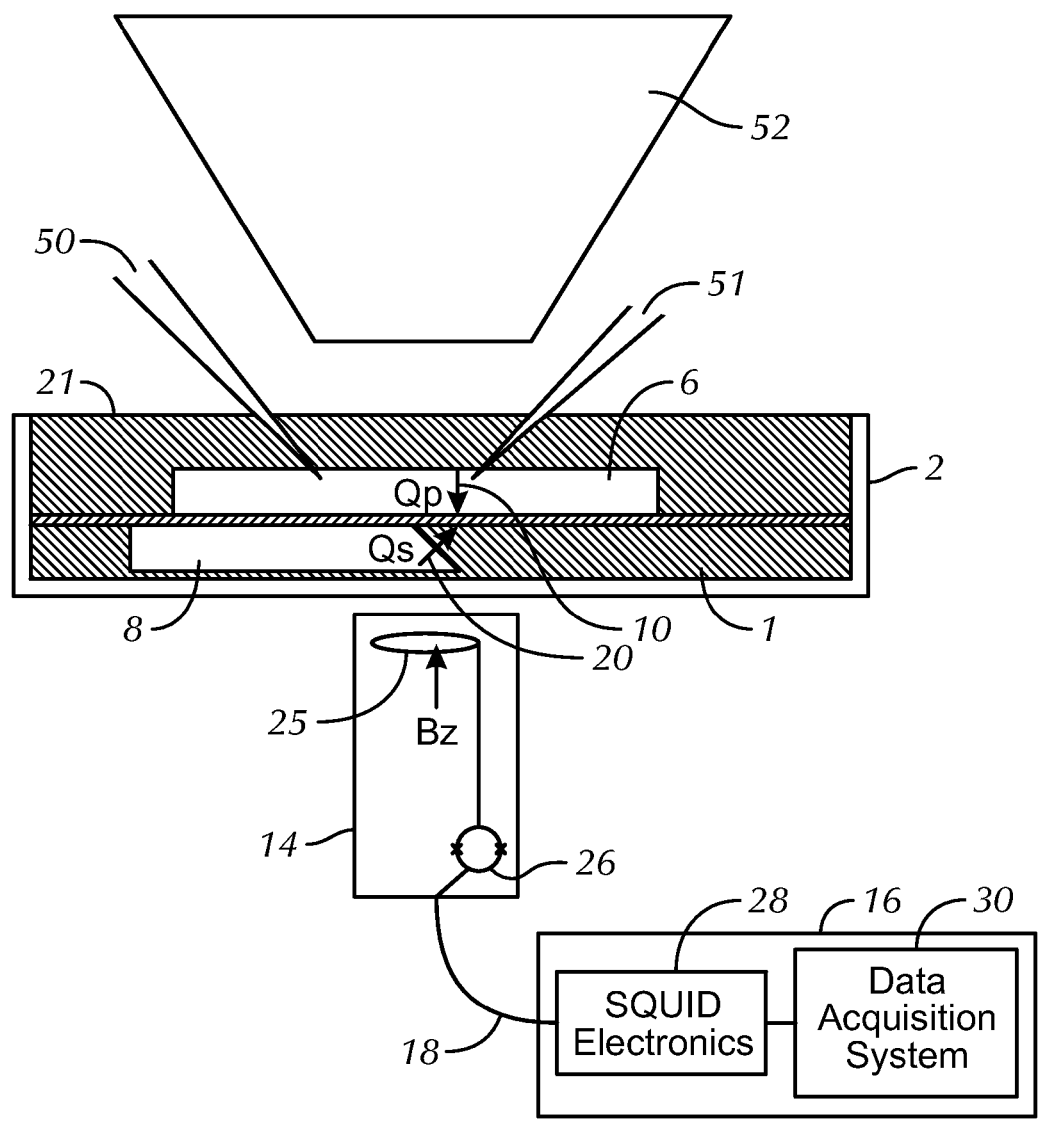
FIG. 4 is a schematic view of the apparatus of FIG. 1 in which the magnetic fields are detected and measured by means of a superconducting magnetometer located below the sample with a conventional optical microscope above the sample to visualize the sample, in accordance with an embodiment of the invention.

Another preferred embodiment of the configuration of FIG. 1 is shown in FIG. 4. In this figure, secondary source 20 in non-conducting solid 8 is produced by primary source 10 in tissue sample 6. All of these structures are immersed in conducting medium 1 in vessel 2 having a boundary surface 21 separating the conducting medium from the non-conductive medium (air). Unlike the previous preferred embodiment shown in FIG. 3, this embodiment makes it possible to measure the magnetic field from the otherwise non-detectable primary source 10 using the magnetometer located below the sample and at the same time visualize the entire tissue sample with conventional optical microscope 52 from above. The neurons in the sample can be stimulated with one or more stimulating electrodes 50. Electrical activity in an individual neuron or a population of neurons can be directly measured with one or more recording electrodes 51, which measure the potentials resulting from the neuronal activity. This configuration increases the versatility and applications of the invention.

The two embodiments in FIG. 3 and FIG. 4 feature a single magnetometer 14. An expanded apparatus can include a large number of magnetometers which can simultaneously detect and measure the magnetic field at many positions produced by a secondary source induced by one primary source. Another expanded embodiment can include multiple non-conductive solids in which secondary sources can be induced by multiple primary sources, with the magnetic fields from all of the secondary sources being detected and measured by all of the multiple magnetometer detector channels.

Figure 5:
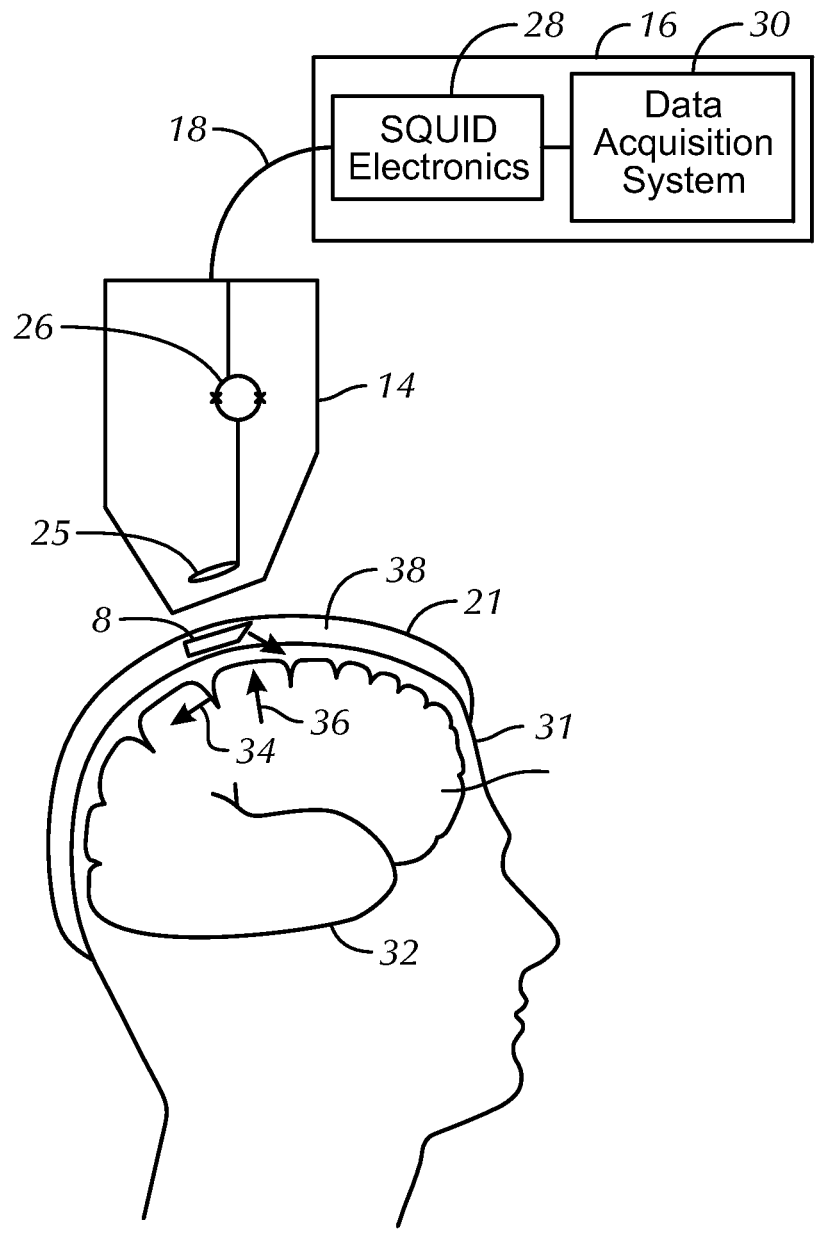
FIG. 5 is a schematic view of an apparatus which enables the enhanced detection of electric currents flowing in the brain of a human being, in accordance with an embodiment of the invention.

The apparatus described above can also be configured with a variety of alternative geometries to suit various applications. The same principles which underlie the embodiments described in detail above will apply, for example, to enhance the ability to measure electric currents flowing within the body of animals or human beings. FIG. 5 shows such an embodiment, which is suitable for measuring the electric currents flowing within the brain 32 of a human being. Large portions of the human brain and head can be modeled as a set of concentric spheres. (See, for example, F. Grynszpan and D. B. Geselowitz, *Model Studies for the Magnetocardiogram*, Biophysics Journal Vol. 13, pp. 911-925 (1973)). The brain itself is a conductive medium containing neuronal structures which carry electric currents. The brain is immersed in the conductive cerebral spinal fluid. The brain is surrounded by the dura, then the skull, and finally the scalp. The last three layers are poor but non-zero conductors. Thus, some currents in the brain, for example, the primary current dipole 36 produced by neurons in the gyrii of the cortex, are oriented perpendicular to the overlying boundary surface separating the head from air. Other currents are oriented tangential to the overlying boundary surface (for example, primary current dipole 34). Conventional magnetoencephalography can measure the magnetic field only from tangential currents such as 34, but not the magnetic field from radial currents such as 36. The invention embodied in FIG. 5 circumvents this fundamental limitation and makes it possible to detect the magnetic field from radial currents 36. In FIG. 5, a conductive gel 38 is spread over the skull, providing another layer of conductive medium. A preferred conductive gel is electroencephalography (EEG) electrode paste. A non-conductive solid 8 of generally cylindrical cross-section and having a flat surface at one end, the plane of which is at an angle of approximately 45 degrees to a plane tangent to the inner surface of the skull, is immersed in the conductive gel. Following the same principles described above, radially oriented primary currents in the brain located close to the PRISM do not produce a magnetic field external to the skull but do induce a secondary source in the PRISM. That secondary source produces a magnetic field which can be detected and measured by magnetometer 14, using the magnetic field detection coil 25 coupled to SQUID 26 which is controlled by SQUID electronics 28, whose output is connected to data acquisition system 30 in box 16. This apparatus in this way enables the detection and measurement of a greater amount of brain electrical activity than is otherwise possible.

The embodiment of FIG. 5 has particular use for examining the brain activity of very young children since, due to poorly developed cortical folding in very premature brains, the brain in the early stages of development contains greater percentages of activity with electric currents flowing in a direction perpendicular to the surface of the skull than in more developed brains. This embodiment is also adapted for when studying the brains of animals with brains containing few sulci and for which most neuronal electrical current flows are perpendicular to the animal's skull.

While particular embodiments of the present invention have been disclosed, it is to be understood that various different modifications and combinations are possible and are contemplated within the true spirit and scope of the disclosed embodiments. There is no intention, therefore, of limitations to the exact disclosures herein presented.

What is claimed is:

1. An apparatus for detecting and measuring the magnetic field produced by a primary electric current source within a conductive biologic structure, the apparatus comprising:
    a conductive medium configured to immerse the biologic structure, the conductive medium being selected from a group consisting of a conductive liquid and a conductive gel, the conductive medium having a first surface;
    a non-conductive solid object fully immersed within the conductive medium, wherein the non-conductive solid object is positioned between the primary electric current source and the first surface, the non-conductive solid object having a surface which is neither parallel nor perpendicular to the first surface of the conductive medium, wherein there is no electrical connection to the non-conductive solid object, and wherein the non-conductive solid object is configured to produce a secondary source responsive to the primary electric current source; and
    a means for detecting and measuring magnetic fields, wherein the detecting and measuring means is located external to the conductive medium.

2. The apparatus of claim 1, wherein the non-conductive solid object has an elongated shape oriented substantially parallel to the first surface of the conductive medium and a substantially flat end surface, the flat end surface positioned proximate to the primary electric current source, wherein the substantially flat surface and the first surface of the conductive medium are at an angle with respect to each other which is between 30 degrees and 60 degrees.

3. The apparatus of claim 1, wherein the non-conductive solid is made from a material selected from the group comprising glass, quartz, sapphire, diamond, reinforced plastic, and non-reinforced plastic.

4. The apparatus of claim 1, and further comprising an optical microscope configured to optically observe the biologic sample concurrently with the detecting and measuring of the magnetic field.

5. The apparatus of claim 1, wherein the conductive liquid is a saline solution.

6. The apparatus of claim 1, wherein a plurality of non-conductive solid objects are fully immersed within the conductive medium and positioned between the primary electric current source and the first surface, each of the non-conductive objects having a surface which is neither parallel nor perpendicular to the first surface of the conductive medium.

7. The apparatus of claim 1, wherein the means for detecting and measuring magnetic fields contains a plurality of magnetometer channels, each of which can detect and measure the magnetic field at a position.

8. The apparatus of claim 1, wherein the means for detecting and measuring magnetic fields is a magnetometer employing a superconducting quantum interference device (SQUID) and superconducting pickup coils.

9. The apparatus of claim 8, and further comprising an optical microscope configured to optically observe the biologic sample concurrently with the detecting and measuring of the magnetic field.

10. An apparatus for detecting and measuring the magnetic field produced by a primary electric current source within a conductive biologic structure having a surface and located in an environment, the apparatus comprising:
    an electrically-conductive gelatinous material configured to cover and contact a portion of the surface of the biologic structure, said gelatinous material having a thickness and having a surface separating it from the environment, the surface being substantially parallel to the surface of the portion of the biologic structure;
    a non-conductive solid object fully immersed within the gelatinous material, wherein the non-conductive solid object is positioned between the primary electric current source and the surface of the gelatinous material, the object having a surface which is neither parallel nor perpendicular to a portion of the surface of the biologic structure, wherein there is no electrical connection to the non-conductive solid object, wherein the non-conductive solid object is configured to produce a secondary source responsive to the primary electric current source; and
    a means for detecting and measuring magnetic fields, the detecting and measuring means being located within the environment.

11. The apparatus of claim 10, wherein the gelatinous material is configured to cover and contact a portion of a head of a human being.

12. The apparatus of claim 10, wherein the gelatinous material is configured to cover and contact a portion of a body of a human being.

13. The apparatus of claim 10, wherein the gelatinous material is configured to cover and contact a portion of an animal.

14. The apparatus of claim 10, wherein the means for detecting and measuring magnetic fields is a SQUID-based magnetometer system.

15. The apparatus of claim 10, wherein the electrically conductive gelatinous material is electroencephalography electrode paste.

16. The apparatus of claim 10, wherein the non-conductive solid is made from a material selected from the group comprising glass, quartz, sapphire, diamond, reinforced plastic, and non-reinforced plastic.

17. A method for detecting and measuring the magnetic field produced by a primary electric current source within a conductive biologic structure located in an environment, the method comprising:
    covering and contacting at least a portion of the biologic structure with a conductive medium being selected from a group consisting of a conductive liquid, a conductive gel, and an electrically-conductive gelatinous material such that the conductive medium is in substantial electrical contact with the biologic structure, the conductive medium having a boundary separating it from the environment;
    fully immersing a non-conductive solid object within the conductive medium, wherein the non-conductive solid object is positioned between the primary electric current source and the boundary, the non-conductive solid object having a surface which is neither parallel nor perpendicular to the boundary, wherein there is no electrical connection to the non-conductive solid object, and wherein the non-conductive solid object is configured to produce a secondary source responsive to the primary electric current source;

placing a means for detecting and measuring magnetic fields within the environment such that the non-conductive solid object is located between the means for detecting and measuring magnetic fields and the biologic structure; and detecting and measuring the magnetic field produced by the secondary sources induced in the non-conductive solid object by the electric currents flowing in the biologic structure.

18. The method of claim 17, the method further comprising placing and configuring an optical microscope to enable optically observing the biologic structure concurrently with measuring the electric currents.

19. The method of claim 17, wherein the conductive medium is a conductive liquid or gel contained in a container and the environment is the air above the surface of the conducting liquid.

20. The method of claim 17, wherein the conductive medium covers and contacts a portion of a head of a human being.

21. The method of claim 17, wherein the means for detecting and measuring magnetic fields is a superconducting quantum interference device (SQUID)-based magnetometer system.

22. The method of claim 17, wherein the conductive medium is an electrically-conductive gelatinous material.

23. The apparatus of claim 10, wherein the means for detecting and measuring magnetic fields contains a plurality of magnetometers.

* * * * *